US008478563B2

(12) United States Patent
Coperet

(10) Patent No.: US 8,478,563 B2
(45) Date of Patent: Jul. 2, 2013

(54) DEVICE AND METHOD FOR THE DIMENSIONAL CHARACTERIZATION OF A CYLINDRICAL OBJECT

(75) Inventor: Philippe Coperet, Meaux (FR)

(73) Assignee: Socomate International, Crecy la Chapelle (FR)

( * ) Notice: Subject to any disclaimer, the term of this patent is extended or adjusted under 35 U.S.C. 154(b) by 970 days.

(21) Appl. No.: 11/569,524

(22) PCT Filed: May 19, 2005

(86) PCT No.: PCT/FR2005/001257
§ 371 (c)(1),
(2), (4) Date: Oct. 11, 2007

(87) PCT Pub. No.: WO2006/000668
PCT Pub. Date: Jan. 5, 2006

(65) Prior Publication Data
US 2008/0059114 A1    Mar. 6, 2008

(30) Foreign Application Priority Data

May 26, 2004    (FR) ...................... 04 05694

(51) Int. Cl.
*G01B 15/02*    (2006.01)
(52) U.S. Cl.
USPC ............... 702/159; 702/81; 702/167; 73/622
(58) Field of Classification Search
USPC ............ 702/81–84, 152, 153, 158, 159, 167, 702/170–172; 73/598, 620–622
See application file for complete search history.

(56) References Cited

U.S. PATENT DOCUMENTS

| | | | | |
|---|---|---|---|---|
| 3,930,404 A | | 1/1976 | Ryden, Jr. | |
| 4,027,527 A | * | 6/1977 | Bennett et al. | 73/622 |
| 4,049,954 A | * | 9/1977 | Da Costa Vieira et al. | 702/157 |
| 4,357,672 A | * | 11/1982 | Howells et al. | 702/159 |
| 4,475,399 A | * | 10/1984 | Livingston | 73/622 |
| 4,740,146 A | * | 4/1988 | Angelbeck | 425/71 |
| 4,976,149 A | * | 12/1990 | Ichikawa et al. | 73/597 |
| 5,063,780 A | * | 11/1991 | Landry et al. | 73/622 |
| 5,156,636 A | * | 10/1992 | Kuljis | 73/597 |

(Continued)

FOREIGN PATENT DOCUMENTS

| | | |
|---|---|---|
| EP | 0304053 | 2/1989 |
| FR | 2234545 | 5/1974 |
| FR | 2833706 | 12/2001 |
| JP | 9184827 | 7/1997 |

OTHER PUBLICATIONS

International Search Report of PCT/FR2005/001257, corresponding to FR 0405694.
French preliminary Search Report of FR 0405694.

*Primary Examiner* — Jeffrey R West
(74) *Attorney, Agent, or Firm* — Patzik, Frank & Samotny Ltd.

(57) ABSTRACT

A device for the dimensional characterization of an object comprising a cylindrical surface which is symmetrical about a longitudinal axle. The device comprises at least six probes used to emit six pulsed waves, each probe being respectively oriented towards a separate measuring point of the cylindrical surface, and to collect the pulsed waves reflected at each measuring point. The device calculates a position of each measuring point, and calculates a characteristic curve of the cylindrical surface by interpolation from the corresponding position of each of the points.

13 Claims, 3 Drawing Sheets

U.S. PATENT DOCUMENTS 5,596,508 A * 1/1997 Cuffe .......................... 702/171
6,000,288 A * 12/1999 Kwun et al. .................. 73/597
2002/0134159 A1 9/2002 He
2005/0156364 A1 7/2005 Bisiaux et al.

* cited by examiner

DEVICE AND METHOD FOR THE DIMENSIONAL CHARACTERIZATION OF A CYLINDRICAL OBJECT

FIELD OF THE INVENTION

The present invention relates to the devices and methods for dimensionally characterizing objects comprising a surface roughly cylindrical of revolution, such as bars or tubes. The present invention also relates to a computer program for implementing a method for dimensionally characterizing such an object.

BACKGROUND OF THE INVENTION

Such devices comprising in particular two probes emitting and collecting ultrasound waves are already known, in particular from documents FR 2 234 545 and U.S. Pat. No. 6,634,233. These ultrasound waves are emitted in pulsed form by the probes, are propagated through an appropriate medium and are reflected by an internal or external surface of the object being studied. These reflected waves then return to a sensor which then generates a signal from which is measured a travel time of the waves in the medium between their emission and their reception after reflection. This travel time, knowing the speed of propagation of the waves in the medium, can be used to calculate the position of the reflection points.

Such devices are normally used to measure the internal and external diameters of a tube and/or the thickness of the wall of such a tube.

SUMMARY OF THE INVENTION

According to one aspect of the present invention, the latter relates to a device for dimensionally characterizing an object comprising a surface that is roughly cylindrical of revolution about a longitudinal axis. This device comprises at least one emitter for emitting at least two pulsed waves. For example, each of these pulsed waves is an acoustic wave. In practice, the inventive device can comprise one probe, typically comprising a piezoelectric crystal, forming both an emitter and a receiver. Thus, each pulsed wave can be emitted by a separate emitter or by one and the same emitter rotating by a certain angle about the longitudinal axis, between the successive emissions of two pulsed waves. Each emission is performed in a medium suitable for propagating these waves, each respectively to a separate measuring point of the cylindrical surface. In this patent application, the expression "measuring point" designates an area of the object, placed on its internal surface or its external surface, which receives and reflects the pulsed waves. This area is not necessarily a point. The inventive device also comprises at least one receiver for collecting the waves reflected, by the cylindrical surface, at each of the measuring points. Furthermore, the inventive device comprises first calculation means for determining the position of each of the measuring points, from the travel time of the pulsed waves over a path comprising a forward section and a return section. The forward section is between each emitter and the corresponding measuring point. The return section is between this measuring point and a receiver. The inventive device further comprises second calculation means, which can be the same as the first calculation means. These second calculation means can be used to reconstruct a portion of the surface or of the cylindrical wall on which is located each of the measuring points, for example in the form of a curve characteristic of this surface. The second calculation means determine this characteristic curve over 360° about the longitudinal axis, passing through each of the measuring points, by interpolation from the corresponding position of each of these points. This characteristic curve represents, for example, the external diameter of a bar or a tube, the internal diameter of a tube or the thickness of a tube wall, under its external surface, or even an ovalization or an excentration of a bar or a tube.

Such an inventive device can be used to determine curves representative of the evolute of a dimensional characteristic of cylindrical objects, from a minimum of measuring points.

In embodiments of the invention, use can, if necessary, also be made of one and/or another of the following arrangements:
- each emitter and each receiver is fixed relative to the object which is moved roughly parallel to the longitudinal axis; the object can thus be checked continuously, without any rotation; this avoids having to apply a double simultaneous rotation and longitudinal travel movement, as in some devices of the prior art in which this double movement is obtained via rollers driving the object, angled, with which high travel speeds of this object cannot be achieved, speeds that are moreover not perfectly controlled because of the slips generated between the rollers and the object;
- each emitter is also a receiver; and
- the device comprises at least four emitters and four receivers, distributed about the object, roughly symmetrically about the longitudinal axis, to determine the position of at least four measuring points; there are thus, for example, six probes, each forming both an emitter and a receiver, 60° apart from each other, about the longitudinal axis.

According to another aspect, the invention relates to a method for dimensionally characterizing an object comprising a surface roughly cylindrical of revolution about a longitudinal axis, such as a bar or a tube, comprising:
- the emission of at least two pulsed waves, in a medium suitable for propagating these waves, each respectively to a separate measuring point of the cylindrical surface,
- the detection of pulsed waves reflected, by the cylindrical surface, at each of the measuring points, and
- the calculation of the position of each of the measuring points, from the travel time of the pulsed waves over a path comprising a forward section between each emitter and the corresponding measuring point and a return section between this measuring point and a receiver, characterized in that it also comprises an operation involving calculating a curve characteristic of the cylindrical surface, over 360° about the longitudinal axis and passing through each of the measuring points, by interpolation from the corresponding position of each of these points.

According to embodiments of this method, use can, if necessary, also be made of one and/or the other of the following arrangements:
- the object is moved roughly parallel to the longitudinal axis;
- the characteristic curve is calculated from the position of at least four measuring points;
- the characteristic curve corresponds to a thickness curve given by:

$$Th = [Th_F \cdot \sin(2\pi t + \phi_F)] + [Th_{2F} \cdot \sin(4\pi t + \phi_{2F})] + Th_{avg}$$

where
- $Th_F$ is the amplitude of the variation of the thickness calculated for an excentration of the object relative to the longitudinal axis, $\phi_F$ is the phase of the variation of the thickness calculated for an excentration of the object relative to the longitudinal axis, $Th_{2F}$ is the amplitude of the variation of the thickness calculated for an ovalization of the object, $\phi_{2F}$ is the phase of the variation of the thickness calculated for an ovalization of the object, $Th_{avg}$ is the average value of the thickness calculated over all the measuring points, t is the sampling period of the interpolated curve;

the characteristic curve corresponds to the external diameter and is given by:

$$\O_{ext}=[\O Ext_{2F}\cdot\sin(4\pi t+\phi Ext_{2F})]+\O_{avg}$$

where $\O Ext_{2F}$ is the amplitude of the variation calculated for the external diameter of the object, $\phi Ext_{2F}$ is the phase of the variation calculated for the external diameter of the object, $\O_{avg}$ is the average value of the diameter calculated over all the measuring points, t is the sampling period of the interpolated curve;

the characteristic curve corresponds respectively to the amplitude and to the phase of the ovalization of the internal diameter and is given by:

$$\text{Modulus}(Ov_{int})=\sqrt{([\text{Sin}(Ov_{int})]^2+(\text{Cos}(Ov_{int})]^2)}=\O Int_{2F}$$

$$\text{Phase}(Ov_{int})=Atg[\text{Sin}(Ov_{int})/\text{Cos}(OV_{int})]=\phi Int_{2F}$$

where $$\text{Sin}(Ov_{int})=(\Sigma Thlnt_i\cdot\sin 2F_i)/(n/2)$$

$$\text{Cos}(Ov_{int})=(\Sigma Thlnt_i\cdot\cos 2F_i)/(n/2)$$

with:

$Thlnt_i=th_i-(\O_i-\O_{avg})$, $\O_{avg}$: the average value of the diameter calculated over all the measuring points, $\O_i$: is a sampling value of the external diameter, $2F_i$ is the ovalization frequency, n equals the number of measuring points;

the emission of the pulsed waves is simultaneous from a set of emitters distributed at roughly equal angles about the longitudinal axis;

the emission of the pulsed waves is performed sequentially over a set of emitters also distributed at roughly equal angles about the longitudinal axis.

According to yet another aspect, the invention relates to a computer program for implementing a method for dimensionally characterizing an object comprising a cylindrical surface that is symmetrical about a longitudinal axis, such as a bar or a tube, this program comprising instructions for:

triggering the emission of at least two pulsed waves by at least one emitter, calculating the position of at least two measuring points, from data collected by at least one receiver and corresponding to a pulsed wave reflected by the cylindrical surface, and calculating a curve characteristic of the cylindrical surface, over 360° about the longitudinal axis and passing through each of the measuring points, by interpolation from the corresponding position of each of these points.

In embodiments of this program, use can, if necessary, also be made of one and/or the other of the following arrangements:

the characteristic curve is calculated based on the position of at least four measuring points;

the characteristic curve corresponds to a thickness curve given by:

$$Th=[Th_F\cdot\sin(2\pi t+\phi_F)]+[Th_{2F}\cdot\sin(4\pi t+\phi_{2F}))]+Th_{avg}$$

where $Th_F$ is the amplitude of the variation of the thickness calculated for an excentration of the object relative to the longitudinal axis, $\phi_F$ is the phase of the variation of the thickness calculated for an excentration of the object relative to the longitudinal axis, $Th_{2F}$ is the amplitude of the variation of the thickness calculated for an ovalization of the object, $\phi_{2F}$ is the phase of the variation of the thickness calculated for an ovalization of the object, $Th_{avg}$ is the average value of the thickness calculated over all the measuring points, t is the sampling period of the interpolated curve;

the characteristic curve corresponds to the external diameter and is given by:

$$\O_{ext}=[\O Ext_{2F}\cdot\sin(4\pi t+\phi Ext_{2F})]+\O_{avg}$$

where $\O Ext_{2F}$ is the amplitude of the variation calculated for the external diameter of the object, $\phi Ext_{2F}$ is the phase of the variation calculated for the external diameter of the object, $\O_{avg}$ is the average value of the diameter calculated over all the measuring points, t is the sampling period of the interpolated curve;

the characteristic curve corresponds respectively to the amplitude and to the phase of the ovalization of the internal diameter and is given by:

$$\text{Modulus}(Ov_{int})=\sqrt{([\text{Sin}(Ov_{int})]^2+(\text{Cos}(Ov_{int})]^2)}=\O Int_{2F}$$

$$\text{Phase}(Ov_{int})=Atg[\text{Sin}(Ov_{int})/\text{Cos}(Ov_{int})]=\phi Int_{2F}$$

where $$\text{Sin}(Ov_{int})=(\Sigma Thlnt_i\cdot\sin 2F_i)/(n/2)$$

$$\text{Cos}(Ov_{int})=(\Sigma Thlnt_i\cdot\cos 2F_i)/(n/2)$$

with:

$Thlnt_i=th_i-(\O_i-\O_{avg})$, $\O_{avg}$: the average value of the diameter calculated over all the measuring points, $\O_i$: is a sampling value of the external diameter, $2F_i$ is the ovalization frequency, n equals the number of measuring points.

Other aspects, objects and advantages of the invention will become apparent from reading the description of one of its embodiments.

BRIEF DESCRIPTION OF THE DRAWINGS

The invention will also be better understood from the drawings, in which.

In the various figures, the same references denote identical or similar elements.

DETAILED DESCRIPTION OF THE INVENTION

Figure 1:
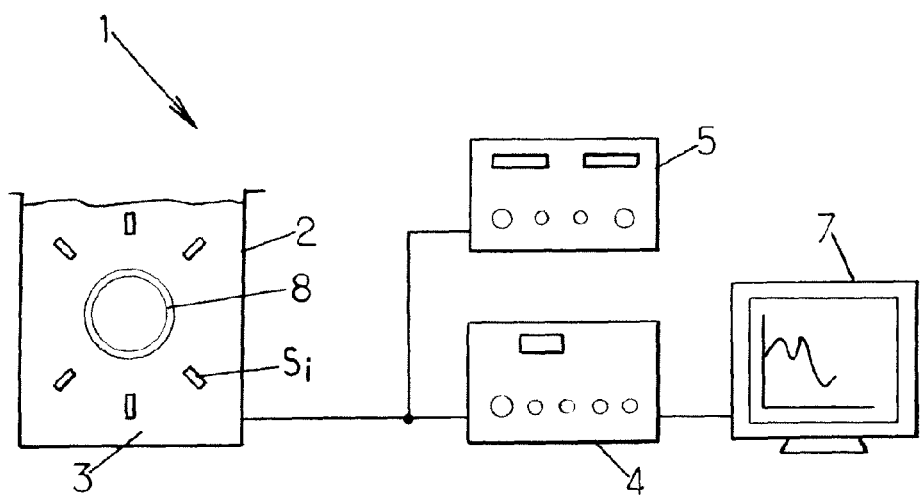
FIG. 1 diagrammatically represents an exemplary device according to the present invention.

An exemplary embodiment of a device 1 according to the invention is represented in FIG. 1. According to this example, the device 1 applies ultrasounds and can be used to measure distances based on the travel time of these ultrasounds. This device 1 comprises a measurement cell 2, calculation means 4, excitation means 5 and display means 7. The measurement cell 2 is filled with a medium 3 suitable for propagating ultrasound waves.

Figure 2:
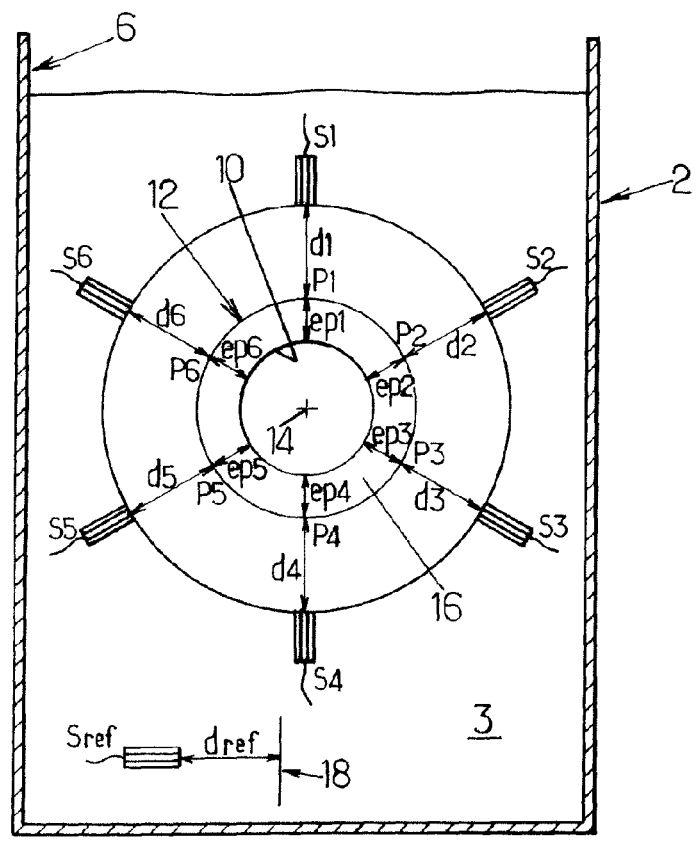
FIG. 2 diagrammatically represents a measuring cell of the device of FIG. 1.

As shown in FIG. 2, the measurement cell comprises a tank 6 commonly called a "water box" by those skilled in the art. In this tank 6 is submerged a tube 8. The tube 8 here constitutes the object for which the dimensional characterization is required. The tube 8 has internal surfaces 10 and external surfaces 12 roughly cylindrical of revolution about a longitudinal axis 14.

Six probes Si with i=1 to 6 are placed roughly symmetrically about the longitudinal axis 14. More specifically, the six probes Si are placed uniformly in steps of 60° about the tube 8 in order to provide a constant angular sampling of the thicknesses Thi with i=1 to 6 and of the distances di with i=1 to 6.

The thicknesses Thi represent the thicknesses of the wall 16 of the tube 8 at six separate measuring points Pi with i=1 to 6. Each of the distances di represents the distance between the probe Si and the corresponding measuring point Pi.

Each probe Si is both an emitter suitable for emitting a pulsed ultrasound wave and a receiver suitable for detecting ultrasound waves propagated through the medium 3. They are, for example, piezoelectric elements.

The accuracy of the positioning of each of the probes Si is not critical. In practice, on the one hand, the distance differences relative to the longitudinal axis 14 can easily be corrected using the calculation means 4 and, on the other hand, the angular position of each probe Si should simply be sufficient to provide an accuracy of 0.1% on the nominal thickness, which in practice allows a positioning error of the order of 1 degree with no problems.

The measurement cell 2 also comprises a probe Sref for measuring the distance dref from a fixed reflector 18 to this probe Sref in order to enable the calculation means 4 to take account of the actual speed of propagation of the ultrasounds in the medium 3 to compensate the di measurements made by the probes Si.

Movement means, not shown, such as a conveyor, move the tube 8 parallel to the longitudinal axis 14.

Figure 3:
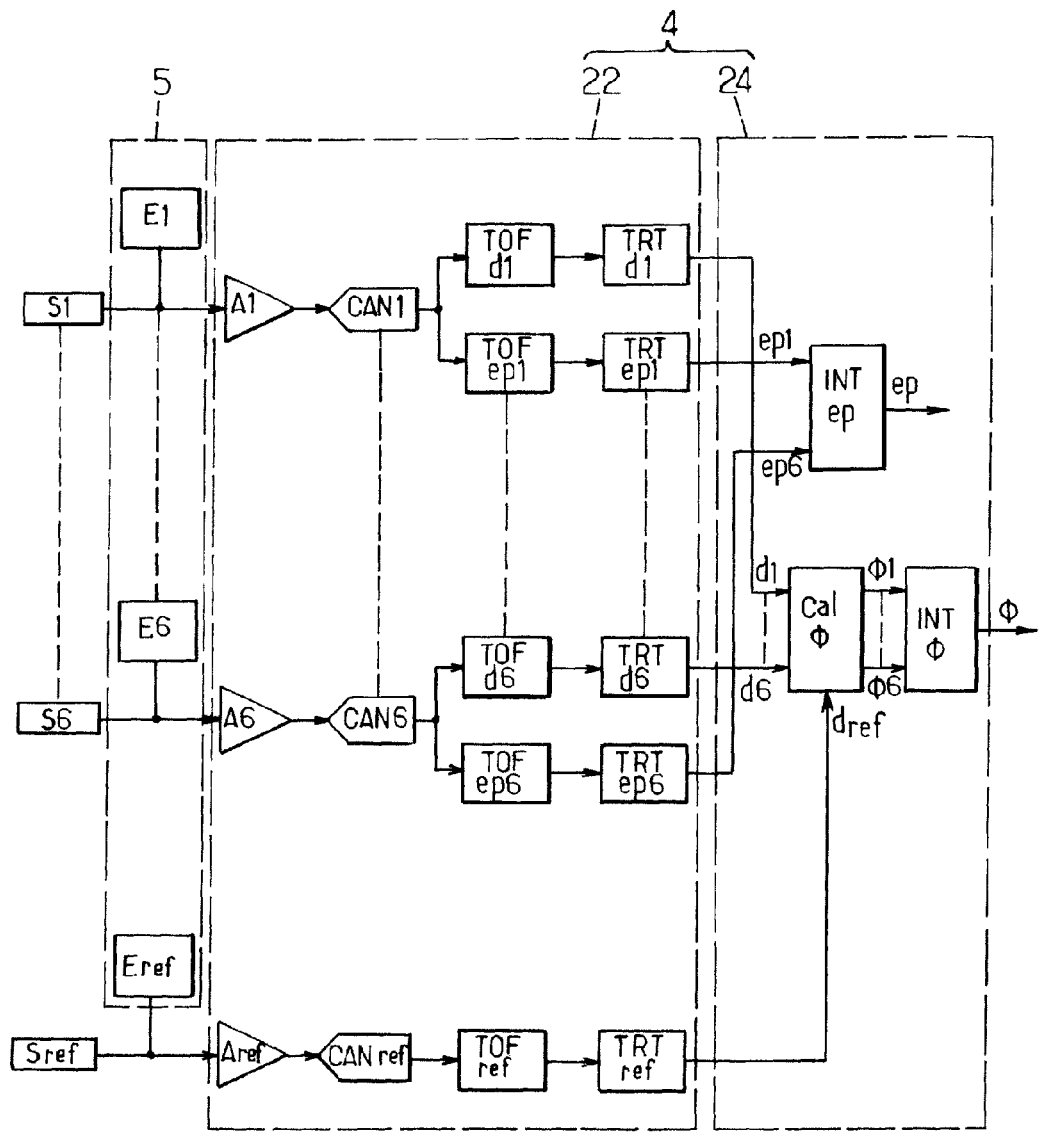
FIG. 3 is a functional diagram of the excitation and calculation means of the device of FIG. 1.

As shown in FIG. 3, the probes Si are connected on the one hand to the calculation means 4 and on the other hand to the excitation means 5.

The excitation means 5 are made up of emitters Ei with i=1 to 6 and Eref. These emitters Ei and Eref generate excitation signals for the probes Si. They advantageously have bandwidths significantly greater than those of the probes Si, so as not to limit the time needed to reach the maximum amplitude of the measuring pulsed waves and thus obtain the best possible accuracy. The emitters Ei and Eref of this type normally have switching times less than 5 nanoseconds, which makes it possible to use probes Si having excitation frequencies that can range up to 25 MHz. These excitation frequencies correspond to the vibration frequencies of the element forming the probes Si.

Moreover, each probe Si generates a measurement signal, in response to the reception of an ultrasound wave. This measurement signal is processed by the calculation means 4.

The calculation means 4 comprise first calculation means 22 and second calculation means 24.

The first calculation means 22 mainly comprise
analog amplifiers Ai with i=1 to 6 and Aref,
analog-digital converters ADCi with i=1 to 6 and ADCref,
period meters TOFdi with i=1 to 6, TOFthi with i=1 to 6 and TOFref, and
filtering circuits TRTdi with i=1 to 6, TRTthi with i=1 to 6 and TRTref.

The analog amplifiers Ai and Aref are intended to condition the signals originating from the probes Si to convert them to the input dynamic range of the converters ADCi and ADCref. For the reasons already explained above, the analog amplifiers Ai and Aref have a bandwidth greater than that of the probes Si.

The converters ADCi and ADCref sample the signals originating from the amplifiers Ai and Aref, with a time resolution compatible with the desired accuracy. In practice, the accuracy on the time measurement defines that of the characteristic curves that are the thickness and diameter curves. In practice, a sampling of between 100 MHz and 200 MHz is sufficient. In practice, the digital processes performed later can improve this resolution still further if necessary.

The period meters TOFdi, TOFthi and TOFref measure the propagation times of the ultrasounds respectively over the distances di, thi and dref. The times corresponding to the distances di are measured between the emission pulse and the reflection echo on the external surface 12 of the tube 8. They therefore correspond to the travel times of the ultrasound waves over a path comprising a forward section between each probe Si and the measuring point Pi, located on the external surface 12 in line with the probe Si, and a return section between this measuring point Pi and the probe Si.

The times corresponding to the thicknesses thi are measured between the reflection echo on the external wall 12 and the reflection echo on the internal wall 10. This corresponds to a synchronization on the so-called input echo, that is, on the external wall 12. This makes it possible to disregard the relative position of the tube 8 relative to the probe Si.

The time corresponding to the distance dref is measured between the emission pulse and the reflection echo on the external surface of the fixed reflector 18.

The circuits TRTdi, TRTthi and TRTref receive the rough time measurements performed by the upstream circuits, in pace with the fired ultrasound waves. This pace is, for example, 5 kHz. The TRTdi, TRTthi and TRTref circuits process the signals that they receive, in real time, according to filtering algorithms that are conventional in the ultrasound field, such as the rejection of aberrant measurements, the filtering of excessively rapid variations between two consecutive measurements and rolling averaging for integrating the measurements. The object of these processes is to eliminate the errored measurements that do not correspond to a physical reality of the method of fabricating the tube 8, so as to transmit error-free data to the second calculation means 24, downstream.

The second calculation means 24 comprise a diameter calculation circuit CALØ, and interpolation circuits INTth and INTØ.

The circuit CALØ calculates, from the distance measurements di, the corresponding diameters of the tube 8. To do this, the di measurements are first of all corrected by a coefficient determined by the dref measurement, in order to compensate for the variations in propagation speed of the ultrasounds in the medium 3.

Each diameter Øi with i=1 to 6 is then calculated for each group of diametrically opposed probes, that is, in pairs S1-S4, S2-S5 and S3-S6.

The interpolation circuits INTth and INTØ interpolate the thickness and diameter characteristic curves, so as to obtain a 96-point resolution per revolution, or an interpolation factor of 16. The interpolation circuits INTth, INTØ can work in the spectral domain, which makes it possible to directly obtain the excentration and ovalization values of the tube 8 from the six sampled measuring points Pi, without having to calculate the interpolated curve.

In the device 1 described above, the number n=6 of probes Si has been chosen for the following reasons.

The period over which the totality of the variation of the distances di due to an excentration is observed corresponds to one revolution of the tube. By contrast, the distance variations observed for an ovalization are observed twice when the tube is revolved once.

Therefore, rather than performing a multitude of measurements around the tube (for example of the order of 100) to obtain a curve representative of the thickness variation (as is the case in certain devices of the prior art), it is enough to sample this curve respecting the SHANNON criterion and to calculate the missing points by interpolation, to construct the complete curve. Remember that, according to the SHANNON criterion, it is necessary for the sampling frequency to be at least equal to twice the highest frequency component of a signal. If this criterion is not respected, an undersampling situation applies which can lead to the appearance of false frequencies.

Thus, for an ovalization, a variation is observed twice for one tube revolution, which means that, according to the SHANNON criterion, at least four measurements per revolution are needed to have an appropriate sampling. The choice of six measurements makes it possible to obtain a redundancy that renders the interpolation more reliable. Thus, certain aberrant measurements can be eliminated without compromising the accuracy of the reconstruction of the characteristic curve sought.

Similarly, this choice of six probes makes it possible to have a sufficient distance between each of the probes for all the measurements to be performed simultaneously. Thus, it is possible to increase the speed with which the tube 8 is checked by a factor of 100 compared to the devices of the prior art which have to perform a hundred or so measurements per revolution to reconstruct a correct curve. However, such an increase in the checking speed is not always necessary, so the measurements can also be performed sequentially so as to reduce the hardware cost. In practice, it is enough to provide for a simplified electronics which, instead of the redundancy by six of the elements constituting the calculation means 4 described above, can be reduced to an example sequentially processing the signals collected on each of the probes Si. This nevertheless makes it possible to retain a considerable increase in the checking speed since it is still 15 times faster with six probes (two opposing probes must necessarily perform their measurements simultaneously to calculate the diameter).

Figure 4:
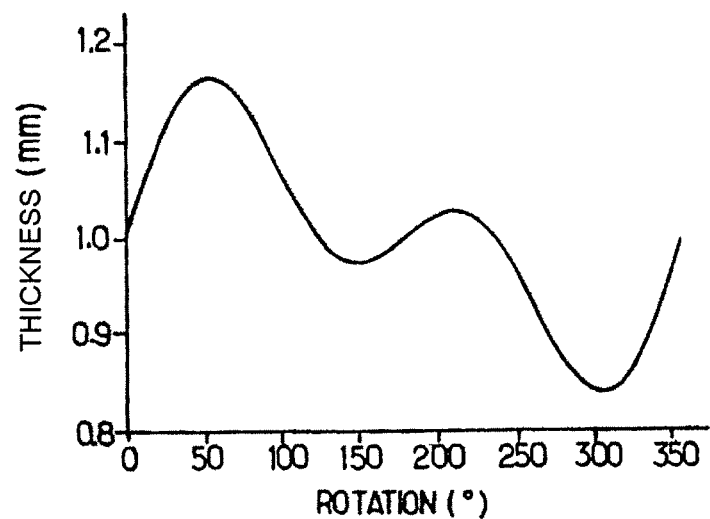
FIG. 4 represents an exemplary interpolated curve corresponding to the thickness variation, over 360°, of a tube.

From six measurements, to reconstruct a curve with a hundred or so points per revolution, which is sufficient to obtain an accuracy of 0.1% over the nominal thickness, the interpolation factor is 16. Such an exemplary curve is represented in FIG. 4.

If the firings are paced at 5 kHz, there are 200 microseconds to perform the interpolation operation. DSP (digital signal processing) circuits can be used for second calculation means 24 because they perform this type of calculation without problems in 200 microseconds.

The interpolation can be done indiscriminately in the time domain by filtering or in the spectral domain by Fourier transform and inverse Fourier transform. One or other of these methods is chosen according to the interpolation factor required.

In practice it is considered, generally, that it is more advantageous to perform the interpolation operation in the time domain if the interpolation factor is less than 64 and it is better to perform in the spectral domain if it is greater than 64.

In practice, if the interpolation factor is high, the number of coefficients for producing the low-pass filter required for the filtering of the interpolation operation in the time domain is great (for example, it is 128 for an interpolation factor of only 16). In this case, the calculation of the Fourier transform and then of the inverse Fourier transform demands less in the way of resources than the convolution processing in the time domain.

Figure 5:
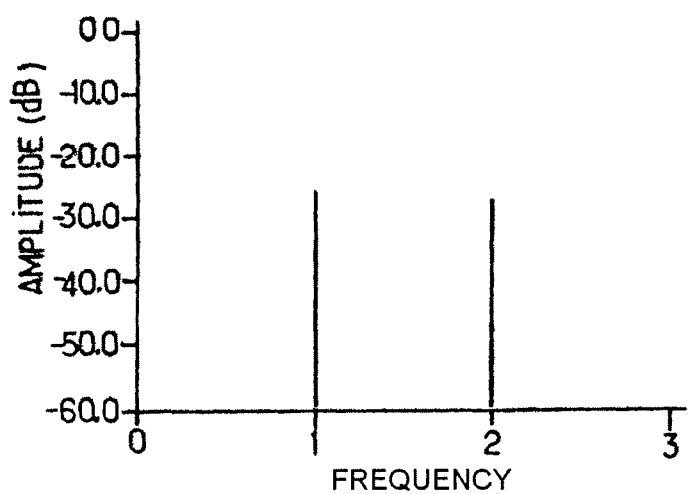
FIG. 5 corresponds to the spectral analysis of the curve represented in FIG. 4.

Moreover, in the spectral domain, it is possible to very easily separate the response due to the excentration from that due to the ovalization (see FIG. 5) by suppressing the spectral ray corresponding to the phenomenon to be eliminated, since we know that both these phenomena respond respectively to frequencies of 1 Hz and 2 Hz.

Thus, without needing the interpolated curve, therefore without the inverse Fourier transform, it is possible to provide the average thickness (continuous ray), the excentration (ray at 1 Hz) and the ovalization (ray at 2 Hz) of a tube, based on points sampled with due regard for the SHANNON criterion.

An example of how to calculate the thickness of a tube 8, and its internal and external diameters, is given below:

I—Thickness

1. To find the phase and the amplitude of the excentration:
the first step consists in multiplying, point by point, the samples $th_i$ acquired with the samples $\sin F_i$ of a sinusoid of period $2\pi$ and calculating the sum of these multiplications to obtain the sine of the excentration (n=number of samples $th_i$).

$$\mathrm{Sin}(Ex) = (\Sigma th_i \cdot \sin F_i)/(n/2)$$

the second step consists in multiplying, point by point, the samples acquired with the samples $\cos F_i$ of the same sinusoid of period $2\pi$ but phase-shifted by $\pi/2$ and in calculating the sum of these multiplications to obtain the cosine of the excentration.

$$\mathrm{Cos}(Ex) = (\Sigma th_i \cdot \cos F_i)/(n/2)$$

All that is then required is to calculate the modulus and the phase based on the Sin(Ex) and Cos(Ex) above, namely:

$$\mathrm{Modulus}(Ex) = \sqrt{([\mathrm{Sin}(Ex)]^2 + [\mathrm{Cos}(Ex)]^2)} = Th_F$$

$$\mathrm{Phase}(Ex) = Atg[\mathrm{Sin}(Ex)/\mathrm{Cos}(Ex)] = \phi_F$$

2. To find the phase and the amplitude of the ovalization:
the principle is the same, but this time the samples $th_i$ acquired are multiplied with the samples $\sin 2F_i$ and $\cos 2F_i$ obtained from a sinusoid of period $4\pi$ of the same phase as the preceding sinusoid of period $2\pi$.
we thus obtain with n=number of samples $th_i$:

$$\mathrm{Sin}(Ov) = (\Sigma th_i \cdot \sin 2F_i)/(n/2)$$

$$\mathrm{Cos}(Ov) = (\Sigma th_i \cdot \cos 2F_i)/(n/2)$$

$$\text{Modulus}(Ov) = \sqrt{([\text{Sin}(Ov)]^2 + (\text{Cos}(Ov))^2)} = Th_{2F}$$

$$\text{Phase}(Ov) = Atg[\text{Sin}(Ov)/\text{Cos}(Ov)] = \phi_{2F}$$

3. To calculate the average thickness value:

$$Th_{avg} = (\Sigma th_i)/n$$

4. To calculate the interpolated thickness curve:

$$Th = [Th_F \cdot \sin(2\pi t + \phi_F)] + [Th_{2F} \cdot \sin(4\pi t + \phi_{2F})] + Th_{avg}$$

With: t=sampling period of the interpolated curve.

II—External Diameter

The principle is the same but is this time applied to the samples $\emptyset_i$ with the period $4\pi$ since we are not trying to find the excentration, which leads, with n=number of samples $\emptyset_I$, to:

$$\text{Sin}(Ov_{ext}) = (\Sigma\emptyset_I \cdot \sin 2F_i)/(n/2)$$

$$\text{Cos}(Ov_{ext}) = (\Sigma\emptyset_I \cdot \cos 2F_i)/(n/2)$$

$$\text{Modulus}(Ov_{ext}) = \sqrt{([\text{Sin}(Ov_{ext})]^2 + (\text{Cos}(Ov_{ext}))^2)} = \emptyset Ext_{2F}$$

$$\text{Phase}(Ov_{ext}) = Atg[\text{Sin}(Ov_{ext})/\text{Cos}(Ov_{ext})] = \phi Ext_{2F}$$

$$\emptyset_{avg} = (\Sigma\emptyset_i)/n$$

$$\emptyset ext = [\emptyset Ext_{2F} \cdot \sin(4\pi t) + \phi Ext_{2F}] + \emptyset_{avg}$$

With: t=sampling period of the interpolated curve

III—Internal Ovalization

The method also makes it possible to extract the ovalization of the internal diameter which is not possible directly from the thickness curve, because the latter restores the vector sum of the internal and external ovalizations.

To do this simply entails subtracting from the samples $th_i$, the corresponding samples $\emptyset_i$ minus $\emptyset_{avg}$, which is tantamount to removing the external ovalization proportion from the thickness.

$$ThInt_i = th_i - (\emptyset_i - \emptyset_{avg})$$

The calculation is then the same as for the external diameter, but with the samples $ThInt_i$ which leads, with n=number of samples $ThInt_i$, to:

$$\text{Sin}(Ov_{int}) = (\Sigma ThInt_i \cdot \sin 2F_i)/(n/2)$$

$$\text{Cos}(Ov_{int}) = (\Sigma ThInt_i \cdot \cos 2F_i)/(n/2)$$

$$\text{Modulus}(Ov_{int}) = \sqrt{([\text{Sin}(Ov_{int})]^2 + (\text{Cos}(Ov_{int}))^2)} = \phi Int_{2F}$$

$$\text{Phase}(Ov_{int}) = Atg[\text{Sin}(Ov_{int})/\text{Cos}(Ov_{int})] = \phi Int_{2F}$$

Knowing the modulus and the phase of the ovalization, the latter is fully determined.

The inventive device described above offers the following main advantages:

- a considerable increase in the checking speeds which can theoretically be as high as a factor of 100; the limit is dictated by the maximum lengthwise travel speed of the tubes allowed by the conveyor;
- the cost of the device is significantly reduced, because it is possible to save on the cost of the rotation means in the case of rotating systems and reduce the number of checking paths by a factor that can be numbered in tens, even hundreds, compared to the case of encircling probes;
- the device is applicable to all types of tubes, large and small, because, on the one hand, the number of probes needed does not depend on the diameter of the tube to be checked, and on the other hand the probes can be installed in a single "water box" as described above for checking small tubes, or in individual "water boxes" in the case of large tubes;
- as indicated above, the positioning of the probes is not absolutely critical for the method itself; the probes must only be adjusted, as in any ultrasound checking system, to obtain correct measurement echos; these adjustments can, moreover, be done very easily since the probes are static and independent; and
- the device makes it possible, through its spectral analysis principle, to separate and directly identify the excentration and ovalization values with their respective phases, which makes it possible to reconstruct the exact profile of the tube for each measured section.

This device applies primarily, but not exclusively, to the dimensional checking by ultrasounds of tubes and bars.

The device is also applicable to the dimensional checking of tubes and bars by any measurement means other than ultrasounds, for example by optical means, by X-rays, and so on.

The device applies generally to the dimensional checking of all products of continuous form with no abrupt variation, performed by any dimensional measurement means.

The invention claimed is:

1. A method for dimensionally characterizing an object, the object comprising a cylindrical surface of revolution about a longitudinal axis, comprising:

emitting at least two pulsed waves, in a medium suitable for propagating these waves, each respectively from an emitter to a separate measuring point of the cylindrical surface, detecting pulsed waves reflected, by the cylindrical surface, at each of the measuring points, calculating a position of and value of a characteristic of the object at each of the measuring points, from a travel time of the at least two pulsed waves over a path comprising a forward section between each emitter and the corresponding measuring point and a return section between the corresponding measuring point and a receiver, and calculating remaining values of the characteristic for a characteristic curve of the cylindrical surface, over 360° about the longitudinal axis by interpolation from the corresponding position of and value of the characteristic at each of the measuring points, the characteristic curve being defined by at least one ovalization parameter, wherein the characteristic curve is calculated based on the position of and values of the characteristic at the measuring points and corresponds to a thickness curve given by:

$$Th = [Th_F \cdot \sin(2\pi t + \phi_F)] + [Th_{2F} \cdot \sin(4\pi t + \phi_{2F})] + Th_{avg}$$

where $Th_F$ is an amplitude of a variation of thickness calculated for an excentration of the object relative to the longitudinal axis and based on the position of and values of the characteristic at the measuring points, $\phi_F$ is a phase of the variation of thickness calculated for an excentration of the object relative to the longitudinal axis and based on the position of and values of the characteristic at the measuring points, $Th_{2F}$ is an amplitude of a variation of thickness calculated for an ovalization of the object and based on the position of and values of the characteristic at the measuring points, $\phi_{2F}$ is a phase of the variation of thickness calculated for an ovalization of the object and based on the position of and values of the characteristic at the measuring points, Th$_{avg}$ is an average value of thickness calculated over all the measuring points, t is a sampling period of the characteristic curve.

2. A method for dimensionally characterizing an object, the object comprising a cylindrical surface of revolution about a longitudinal axis, comprising:

emitting at least two pulsed waves, in a medium suitable for propagating these waves, each respectively from an emitter to a separate measuring point of the cylindrical surface, detecting pulsed waves reflected, by the cylindrical surface, at each of the measuring points, calculating a position of and value of a characteristic of the object at each of the measuring points, from a travel time of the at least two pulsed waves over a path comprising a forward section between each emitter and the corresponding measuring point and a return section between the corresponding measuring point and a receiver, and calculating remaining values of the characteristic for a characteristic curve of the cylindrical surface, over 360° about the longitudinal axis by interpolation from the corresponding position of and value of the characteristic at each of the measuring points, the characteristic curve being defined by at least one ovalization parameter, wherein the characteristic curve is calculated based on the position of and values of the characteristic at the measuring points and corresponds to an external diameter given by:

$$\O_{ext} = [\O Ext_{2F} \cdot \sin(4\pi t + \phi Ext_{2F})] + \O_{avg}$$

where $\O Ext_{2F}$ is an amplitude of a variation calculated for the external diameter of the object and calculated based on the position of and values of the characteristic at the measuring points, $\phi Ext_{2F}$ is a phase of the variation calculated for the external diameter of the object and calculated based on the position of and values of the characteristic at the measuring points, $\O_{avg}$ is an average value of the external diameter calculated over all the measuring points, t is a sampling period of the characteristic curve.

3. A method for dimensionally characterizing an object, the object comprising a cylindrical surface of revolution about a longitudinal axis, comprising:

emitting at least two pulsed waves, in a medium suitable for propagating these waves, each respectively from an emitter to a separate measuring point of the cylindrical surface, detecting pulsed waves reflected, by the cylindrical surface, at each of the measuring points, calculating a position of and value of a characteristic of the object at each of the measuring points, from a travel time of the at least two pulsed waves over a path comprising a forward section between each emitter and the corresponding measuring point and a return section between the corresponding measuring point and a receiver, and calculating remaining values of the characteristic for a characteristic curve of the cylindrical surface, over 360° about the longitudinal axis by interpolation from the corresponding position of and value of the characteristic at each of the measuring points, the characteristic curve being defined by at least one ovalization parameter, wherein the characteristic curve is calculated based on the position of and values of the characteristic at the measuring points and corresponds respectively to an amplitude and to a phase of an ovalization of an internal diameter given by:

$$\text{Modulus}(Ov_{int}) = \sqrt{([(\Sigma Thlnt_i \cdot \sin 2F_i)/(n/2)]^2 + [(\Sigma Thlnt_i \cdot \cos 2F_i)/(n/2)]^2)} = \O Int_{2F}$$

$$\text{Phase}(Ov_{int}) = Atg[((\Sigma Thlnt_i \cdot \sin 2F_i)/(n/2))/((\Sigma Thlnt_i \cdot \cos 2F_i)/(n/2))] = \phi Int_{2F}$$

with:

$Thlnt_i = th_i - (\O_i - \O avg)$, $th_i$ is a sampling value of a thickness of a wall of the object based on the values of the characteristic at the measuring points, $\O_{avg}$: is an average value of the external diameter calculated over all the measuring points, $\O_i$ is an external diameter sampling value of the values of the characteristic at the measuring points, $2F_i$ is an ovalization frequency based on the position of the measuring points, n equals a number of measuring points.

4. A device for dimensionally characterizing an object, the object comprising a cylindrical surface of revolution about a longitudinal axis, comprising:

at least one emitter for emitting at least two pulsed waves, in a medium suitable for propagating these waves, each respectively to a separate measuring point of the cylindrical surface, at least one receiver for collecting pulsed waves reflected, by the cylindrical surface, at each of the measuring points, and first means of calculating a position of and a value of a characteristic of the object at each of the measuring points, based on a travel time of the at least two pulsed waves over a path comprising a forward section between each emitter and the corresponding measuring point and a return section between the corresponding measuring point and a receiver, and second means of calculating remaining values of the characteristic for a characteristic curve of the cylindrical surface, over 360° about the longitudinal axis by interpolation from the corresponding position of and value of the characteristic at each of the measuring points, the characteristic curve is calculated based on the position of and values of the characteristic at the measuring points and corresponding to one of:

a) a thickness curve given by:

$$Th = [Th_F \cdot \sin(2\pi t + \phi_F)] + [Th_{2F} \cdot \sin(4\pi t + \phi_{2F})] + Th_{avg}$$

where $Th_F$ is an amplitude of a variation of thickness calculated for an excentration of the object relative to the longitudinal axis and based on the position of and values of the characteristic at the measuring points, $\phi_F$ is a phase of the variation of thickness calculated for an excentration of the object relative to the longitudinal axis and based on the position of and values of the characteristic at the measuring points, $Th_{2F}$ is an amplitude of a variation of thickness calculated for an ovalization of the object and based on the position of and values of the characteristic at the measuring points, $\phi_{2F}$ is a phase of the variation of thickness calculated for an ovalization of the object and based on the position of and values of the characteristic at the measuring points, $Th_{avg}$ is an average value of the thickness calculated over all the measuring points, t is a sampling period of the characteristic curve; and b) an external diameter given by:

$$\O_{ext}=[\O Ext_{2F}\cdot\sin(4\pi t+\phi Ext_{2F})]+\O_{avg}$$

where
- $\O Ext_{2F}$ is an amplitude of a variation calculated for the external diameter of the object and based on the position of and values of the characteristic at the measuring points,
- $\phi Ext_{2F}$ is a phase of the variation calculated for the external diameter of the object and based on the position of and values of the characteristic at the measuring points,
- $\O_{avg}$ is an average value of the external diameter calculated over all the measuring points,
- t is a sampling period of the characteristic curve; and c) an amplitude and a phase of an ovalization of an internal diameter, given by:

$$Modulus(Ov_{int})=\sqrt{([(\Sigma Th Int_i\cdot\sin 2F_i)/(n/2)]^2+[(\Sigma Th Int_i\cdot\cos 2F_i)/(n/2)]^2)}=\O Int_{2F}$$

$$Phase(Ov_{int})=Atg[((\Sigma Th Int_i\cdot\sin 2F_i)/(n/2))/((\Sigma Th Int_i\cdot\cos 2F_i)/(n/2))]=\phi Int_{2F}$$

with:
- $Th Int_i=th_i-(\O_i-\O_{avg})$,
- $th_i$: is a sampling value of a thickness of a wall of the object based on the values of the characteristic at the measuring points,
- $\O_{avg}$: is an average value of the external diameter calculated over all the measuring points,
- $\O_i$: is an external diameter sampling value of the values of the characteristic at the measuring points,
- $2F_i$ is an ovalization frequency based on the position of the measuring points,
- n equals a number of measuring points.

5. The device as claimed in claim 4, wherein each at least one emitter and each at least one receiver is fixed relative to the object which is moved parallel to the longitudinal axis.

6. The device as claimed in claim 4, wherein each at least one emitter is also a receiver.

7. The device as claimed in claim 4, wherein the at least one emitter is one of four and six emitters.

8. The device as claimed in claim 4, comprising at least four emitters and four receivers, distributed about the object symmetrically about the longitudinal axis, to determine the position of at least four measuring points.

9. A method for dimensionally characterizing an object, the object comprising a cylindrical surface of revolution about a longitudinal axis, comprising:
- emitting at least two pulsed waves, in a medium suitable for propagating these waves, each respectively from an emitter to a separate measuring point of the cylindrical surface,
- detecting pulsed waves reflected, by the cylindrical surface, at each of the measuring points, and
- calculating a position of and a value of a characteristic of the object at each of the measuring points, from a travel time of the at least two pulsed waves over a path comprising a forward section between each emitter and the corresponding measuring point and a return section between the corresponding measuring point and a receiver, and
- calculating remaining values of the characteristic for a characteristic curve of the cylindrical surface, over 360° about the longitudinal axis by interpolation from the corresponding position of and value of the characteristic at each of the measuring points, the characteristic curve is calculated based on the position of and values of the characteristic at the measuring points and corresponding to one of:

a) a thickness curve given by:

$$Th=[Th_F\cdot\sin(2\pi t+\phi_F)]+[Th_{2F}\cdot\sin(4\pi t+\phi_{2F})]+Th_{avg}$$

where
- $Th_F$ is an amplitude of a variation of thickness calculated for an excentration of the object relative to the longitudinal axis and based on the position of and values of the characteristic at the measuring points,
- $\phi_F$ is a phase of the variation of the thickness calculated for an excentration of the object relative to the longitudinal axis and based on the position of and values of the characteristic at the measuring points,
- $Th_{2F}$ is an amplitude of a variation of the thickness calculated for an ovalization of the object and based on the position of and values of the characteristic at the measuring points,
- $\phi_{2F}$ is a phase of the variation of the thickness calculated for an ovalization of the object and based on the position of and values of the characteristic at the measuring points,
- $Th_{avg}$ is an average value of the thickness calculated over all the measuring points,
- t is a sampling period of the characteristic curve; and b) an external diameter given by:

$$\O_{ext}=[\O Ext_{2F}\cdot\sin(4\pi t+\phi Ext_{2F})]+\O_{avg}$$

where
- $\O Ext_{2F}$ is an amplitude of a variation calculated for the external diameter of the object and based on the position of and values of the characteristic at the measuring points,
- $\phi Ext_{2F}$ is a phase of the variation calculated for the external diameter of the object and based on the position of and values of the characteristic at the measuring points,
- $\O_{avg}$ is an average value of the external diameter calculated over all the measuring points,
- t is a sampling period of the characteristic curve; and c) an amplitude and a phase of an ovalization of an internal diameter, given by:

$$Modulus(Ov_{int})=\sqrt{([(\Sigma Th Int_i\cdot\sin 2F_i)/(n/2)]^2+[(\Sigma Th Int_i\cdot\cos 2F_i)/(n/2)]^2)}=\O Int_{2F}$$

$$Phase(Ov_{int})=Atg[((\Sigma Th Int_i\cdot\sin 2F_i)/(n/2))/((\Sigma Th Int_i\cdot\cos 2F_i)/(n/2))]=\phi Int_{2F}$$

with:
- $Th Int_i=th_i-(\O_i-\O_{avg})$,
- $th_i$: is a sampling value of a thickness of a wall of the object based on the values of the characteristic at the measuring points,
- $\O_{avg}$: an average value of the external diameter calculated over all the measuring points,
- $\O_i$: is an external diameter sampling value of the values of the characteristic at the measuring points,
- $2F_i$ is an ovalization frequency based on the position of the measuring points,
- n equals a number of measuring points.

10. The method as claimed in claim 9, wherein the object is moved parallel to the longitudinal axis.

11. The method as claimed in claim 9, wherein the characteristic curve is calculated from the position of at least four measuring points.

12. The method as claimed in claim 9, wherein the emission of the at least two pulsed waves is simultaneous from a set of emitters distributed at equal angles about the longitudinal axis.

13. The method as claimed in claim 9, wherein the emission of the at least two pulsed waves is performed sequentially over a set of emitters distributed at equal angles about the longitudinal axis.

* * * * *